United States Patent
Jin et al.

(10) Patent No.: US 12,092,604 B2
(45) Date of Patent: Sep. 17, 2024

(54) SYSTEMS AND RELATED METHODS FOR ANALYZING A GAS

(71) Applicant: Applied Nanotools Inc., Edmonton (CA)

(72) Inventors: Cong Jin, Edmonton (CA); Samuel Mukasa Muwanguzi, Edmonton (CA); Cameron Steve Horvath, Edmonton (CA); Mirwais Aktary, Edmonton (CA)

(73) Assignee: APPLIED NANOTOOLS INC., Edmonton (CA)

( * ) Notice: Subject to any disclaimer, the term of this patent is extended or adjusted under 35 U.S.C. 154(b) by 200 days.

(21) Appl. No.: 17/574,608

(22) Filed: Jan. 13, 2022

(65) Prior Publication Data

US 2022/0236216 A1   Jul. 28, 2022

Related U.S. Application Data

(60) Provisional application No. 63/141,548, filed on Jan. 26, 2021.

(30) Foreign Application Priority Data

Dec. 6, 2021   (CA) ................................ CA 3141116

(51) Int. Cl.
  *G01N 27/416*   (2006.01)
  *G01N 1/34*   (2006.01)
(52) U.S. Cl.
  CPC .......... *G01N 27/4162* (2013.01); *G01N 1/34* (2013.01)

(58) Field of Classification Search
  CPC .. G01N 27/4162; G01N 33/0044; G01N 1/34; G01N 33/0014
  See application file for complete search history.

(56) References Cited

U.S. PATENT DOCUMENTS

| | | |
|---|---|---|
| 4,526,755 A | 7/1985 | Vincent et al. |
| 5,654,498 A | 8/1997 | Kessel |
| 7,060,169 B2 | 6/2006 | Rohrl |
| 9,126,893 B2 | 9/2015 | Rohrl |

(Continued)

FOREIGN PATENT DOCUMENTS

| | | |
|---|---|---|
| EP | 0445927 A2 | 9/1991 |
| JP | H11258199 A | 9/1999 |

(Continued)

OTHER PUBLICATIONS

Machine English Translation of WO 2020/241768 (Year: 2020).*

(Continued)

*Primary Examiner* — Gurpreet Kaur
(74) *Attorney, Agent, or Firm* — Schmeiser, Olsen & Watts, LLP

(57) ABSTRACT

Systems and methods for analyzing a gas are provided. In some embodiments, the system includes: at least one scrubber including a scrubber material that removes at least one sulfur compound from the gas to produce a scrubbed gas; at least one gas sensor in fluid communication with the at least one scrubber, the at least one gas sensor sensing at least one remaining sulfur compound in the scrubbed gas. In some embodiments, the systems and methods disclosed herein may be used to analyze individual odorants in a hydrocarbon gas such as natural gas.

16 Claims, 11 Drawing Sheets

(56) References Cited

U.S. PATENT DOCUMENTS

| | | |
|---|---|---|
| 9,126,894 B2 | 9/2015 | Rohrl |
| 10,379,093 B2 | 8/2019 | Murphy et al. |
| 10,509,007 B1 * | 12/2019 | Henshaw .................. G01N 1/18 |
| 2011/0156714 A1 | 6/2011 | Mizoguchi et al. |
| 2017/0176378 A1 * | 6/2017 | Otjes .................. G01N 33/0024 |

FOREIGN PATENT DOCUMENTS

| | | | |
|---|---|---|---|
| WO | 2020183203 A1 | 9/2020 | |
| WO | WO-2020241768 A1 * | 12/2020 | ......... G01N 21/3103 |

OTHER PUBLICATIONS

Macak et al. "Determination of sulphur compounds in natural gas by gas chromatography with a flame photometric detector", Journal of Chromatography, 286 (1984), pp. 69-78.

Guth et al. "Recent developments in electrochemical sensor application and technology—a review", Measurement Science and Technology, 20 (2009), 042002.

* cited by examiner

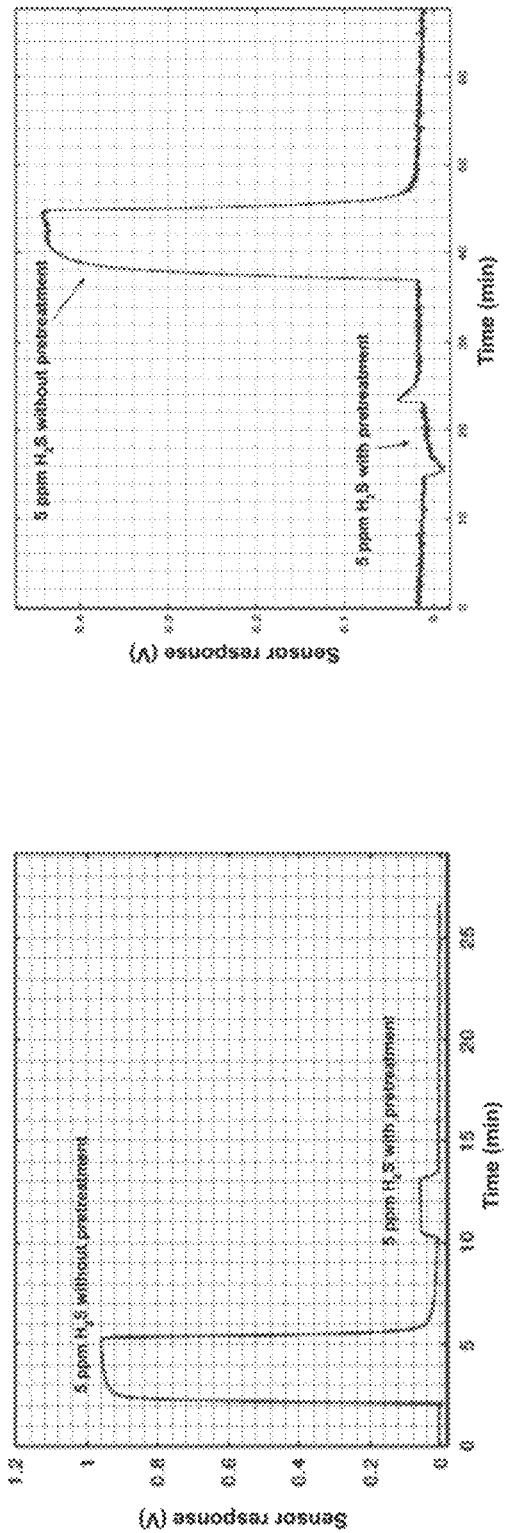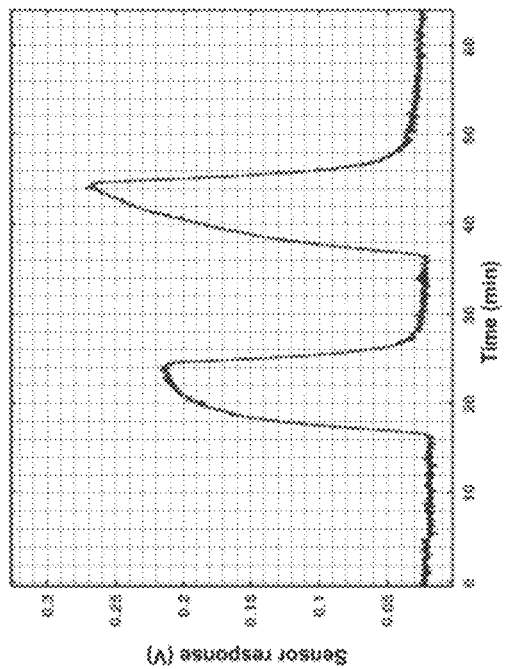

SYSTEMS AND RELATED METHODS FOR ANALYZING A GAS

CROSS-REFERENCE TO RELATED APPLICATION

This application claims priority to U.S. Provisional Patent Application No. 63/141,548, having a filing date of Jan. 26, 2021, and Canadian Patent Application No. 3,141,116, having a filing date of Dec. 6, 2021, the entire contents both of which are incorporated herein by reference.

FIELD OF TECHNOLOGY

The following relates to gas analysis. More particularly, the present disclosure relates to systems and methods for analyzing sulfur compounds in hydrocarbon gas.

BACKGROUND

Hydrocarbon gases including natural gas, liquid petroleum gas, and propane are colorless and odorless. Organosulfur compounds are typically used to odorize hydrocarbon gases, allowing humans to detect leakage of these hydrocarbons before they reach their lower explosion limit. Organosulfur compounds commonly used as gas odorants include tetrahydrothiophene (THT), tert-butyl mercaptan (TBM), ethyl mercaptan (EM), sec-butyl mercaptan (SBM), methyl ethyl sulfide (MES), n-propyl mercaptan (NPM), isopropyl mercaptan (IPM), diethyl sulfide (DES), and dimethyl sulfide (DMS). In North America, a widely used natural gas odorant is a blend of TBM and MES.

Natural gas distributors typically analyze and maintain the concentration of the odorants throughout their distribution network on a regular basis. This process is conventionally done by sampling natural gas samples from the field and sending each sample to a gas chromatography laboratory for analysis. An example of natural gas odorant analysis method with gas chromatography can be found in Macak et al. "Determination of sulphur compounds in natural gas by gas chromatography with a flame photometric detector", Journal of Chromatography, 286 (1984), pp. 69-78. However, such methods can be time-consuming and expensive.

U.S. Pat. No. 4,526,755 to Vincent et al. teaches an alternative approach to natural gas odorant analysis in which natural gas passes through bubblers followed by analysis by coulometric titrators. The bubblers contain aqueous solutions to remove specific compounds from the natural gas: e.g., a 1.0% $CdSO_4$ and 2.0% $H_3BO_3$ solution (to remove $H_2S$), a 10.0% NaOH solution (to remove mercaptans), and a 0.5% $AgNO_3$ water solution (to remove sulfides). Although this approach may be suitable for laboratory use, it is not suitable for field deployment as the aqueous bubbling solutions may freeze if the environmental temperature drops below their freezing point. The concentration of the bubbling solutions may also need to be frequently compensated due to evaporation. Furthermore, additional moisture in the processed gas can also influence the performance of the sensors positioned downstream of the bubblers.

Another possible approach for the analysis of odorants in natural gas involves the use of electrochemical cell gas sensors, also known as electrochemical sensors. Electrochemical sensors are widely used and their selectivity has improved greatly over in recent years (Guth et al. "Recent developments in electrochemical sensor application and technology—a review", Measurement Science and Technology, 20 (2009), 042002); however, they still suffer from cross-sensitivity issues. For example, an electrochemical sensor designed for sensing methyl mercaptan (MM) will also respond to other sulfur-containing molecules (including TBM, MES, and $H_2S$), triggering a false positive when MM is not present. Thus, electrochemical gas sensors alone are not able to analyze the concentrations of individual odorants when two or more sulfur compounds are present in an analyte gas. As a result, commercial electrochemical gas sensors designed for natural gas odorant analysis typically only provide estimated total odorant concentration. In addition, these sensors may be affected by cross-sensitivity to $H_2S$ that naturally exists in natural gas.

European Patent Publication No. EP0445927 to Willance et al. describes an odorant analyzer system to address the cross-sensitivity issue. The system utilizes a gas chromatography column to separate the sulfur compounds present in a natural gas sample before analysis by an electrochemical gas sensor. However, this system is large and complex with considerable electronic requirements, which would be difficult to implement for field deployment in hazardous locations.

SUMMARY

An aspect relates to a system for analyzing a gas, the system comprising: at least one scrubber comprising a non-aqueous scrubber material that removes at least one sulfur compound from the gas to produce a scrubbed gas; and at least one gas sensor in fluid communication with the at least one scrubber, the at least one gas sensor sensing at least one remaining sulfur compound in the scrubbed gas.

In some embodiments, the scrubber material comprises an alkali metal hydroxide, an alkaline earth metal hydroxide, a carbonate salt, a bicarbonate salt, an iodate salt, a metal oxide, an amine, or a combination thereof.

In some embodiments, the at least one scrubber comprises a first scrubber and a second scrubber, the first scrubber comprising a first scrubber material and the second scrubber comprising a second scrubber material.

In some embodiments, the first scrubber material is a liquid-phase scrubber material and the second scrubber material is a solid-phase scrubber material.

In some embodiments, the first scrubber material comprises at least one of a carbonate salt, a bicarbonate salt, a metal oxide, and an amine, and the second scrubber material comprises at least one of an alkali metal hydroxide, an alkaline earth metal hydroxide, and an iodate salt.

In some embodiments, the at least one gas sensor comprises a first gas sensor and a second gas sensor, the first gas sensor fluidly connected to the first scrubber and the second gas sensor fluidly connected to the second scrubber.

In some embodiments, the system further comprises a valve in fluid communication with the first and second scrubbers and the at least one gas sensor, the valve selectively movable between a first position in which a first gas stream flows from the first scrubber to the at least one gas sensor and a second position in which a second gas stream flows from the second scrubber to the at least one gas sensor.

In some embodiments, the system further comprises at least one pump operable to move the scrubbed gas from the at least one scrubber to the at least one gas sensor.

In some embodiments, the system further comprises a processor that processes sensor output of the at least one gas sensor to determine a concentration of the at least one remaining sulfur compound.

In some embodiments, the at least one gas sensor comprises one or more electrochemical cells.

In another aspect, there is provided a method for analyzing a gas, the method comprising: contacting the gas with a non-aqueous scrubber material that removes at least one sulfur compound to produce a scrubbed gas; and sensing at least one remaining sulfur compound in the scrubbed gas.

In some embodiments, the scrubber material comprises at least one of a carbonate salt, a bicarbonate salt, a metal oxide, and an amine.

In some embodiments, sensing the at least one remaining sulfur compound comprises sensing at least one of tetrahydrothiophene (THT), tert-butyl mercaptan (TBM), methyl ethyl sulfide (MES), n-propyl mercaptan (NPM), isopropyl mercaptan (IPM), dimethyl sulfide (DMS), sec-butyl mercaptan (SBM), diethyl sulfide (DES), and ethyl mercaptan (EM).

In some embodiments, sensing the at least one remaining sulfur compound comprises sensing a first sulfur content of the scrubbed gas.

In some embodiments, further comprising sensing a second sulfur content of an unscrubbed stream of the gas and determining an $H_2S$ concentration based on the difference between the first sulfur content and the second sulfur content.

In some embodiments, the scrubber material comprises at least one of an alkali metal hydroxide, an alkaline earth metal hydroxide, and an iodate salt.

In some embodiments, sensing the at least one remaining sulfur compound comprises sensing at least one of MES, DMS, DES, and THT.

In some embodiments, the at least one remaining sulfur compound is sensed by at least one gas sensor, the at least one gas senor comprising one or more electrochemical cells.

In another aspect, there is provided a method for analyzing a gas, the method comprising: separating the gas into a first gas stream and a second gas stream; contacting the first gas stream with a first non-aqueous scrubber material to produce a first scrubbed gas stream; contacting the second gas stream with a second non-aqueous scrubber material to produce a second scrubbed gas stream; sensing at least one first remaining sulfur compound in the first scrubbed gas stream; and sensing at least one second remaining sulfur compound in the second scrubbed gas stream.

In some embodiments, the first scrubber material comprises at least one of a carbonate salt, a bicarbonate salt, a metal oxide, and an amine, and the second scrubber material comprises at least one of an alkali metal hydroxide, an alkaline earth metal hydroxide, and an iodate salt.

Other aspects and features of the present disclosure will become apparent, to those ordinarily skilled in the art, upon review of the following description of the specific embodiments of the disclosure.

BRIEF DESCRIPTION

Some of the embodiments will be described in detail, with references to the following Figures, wherein like designations denote like members, wherein:

FIG. 15A is a line graph showing electrochemical sensor output in response to $H_2S$, with or without a pre-treatment step with $CaCO_3$ scrubber material and MDEA scrubber material, respectively;

FIG. 15B is a line graph showing electrochemical sensor output in response to $H_2S$, with or without a pre-treatment step with $CaCO_3$ scrubber material and MDEA scrubber material, respectively; and FIG. 16 is a line graph showing electrochemical sensor output in response to a gas sample comprising TBM, MES, and $H_2S$ following a pre-treatment step with NaOH and $Ca(OH)_2$ scrubber material (first peak) or MDEA scrubber material (second peak).

DETAILED DESCRIPTION

Generally, the present disclosure provides a system for analyzing a gas. In some embodiments, the system comprises: at least one scrubber comprising a non-aqueous scrubber material that removes at least one sulfur compound from the gas; at least one gas sensor in fluid communication with the at least one scrubber, the at least one gas sensor sensing at least one remaining sulfur compound in the scrubbed gas. Related methods for analyzing a gas are also provided.

As used herein, "upstream" and "downstream" refer to the direction of flow of a gas stream through embodiments of the systems described herein. Under normal operating conditions, the gas stream flows from an upstream position to a downstream position.

The systems and methods disclosed herein may be used to analyze a gas. In some embodiments, the gas is a hydrocarbon gas. As used herein, the term "hydrocarbon gas" refers to any gas comprising at least one hydrocarbon component. Non-limiting examples of hydrocarbon gases include natural gas, liquefied petroleum gas, and propane. In some embodiments, the gas further comprises one or more native sulfur compounds that are naturally present in the gas. In some embodiments, the native sulfur compounds comprise hydrogen sulfide ($H_2S$) and/or one or more mercaptans.

The gas may further comprise one or more odorants. In some embodiments, one or more of the odorants comprises a sulfur compound. In some embodiments, the sulfur compound is an organosulfur compound. Non-limiting examples of organosulfur compounds include (THT), tert-butyl mercaptan (TBM), ethyl mercaptan (EM), sec-butyl mercaptan (SBM), methyl ethyl sulfide (MES), n-propyl mercaptan (NPM), isopropyl mercaptan (IPM), diethyl sulfide (DES), and dimethyl sulfide (DMS). In some embodiments, the gas comprises a blend of two or more odorants including, but not limited to, an organic sulfide and a mercaptan (e.g., TBM/MES blends or TBM/THT blends). In some embodiments, the gas to be analyzed comprises between about 0 and about 10 ppm of each odorant.

Figure 1A:
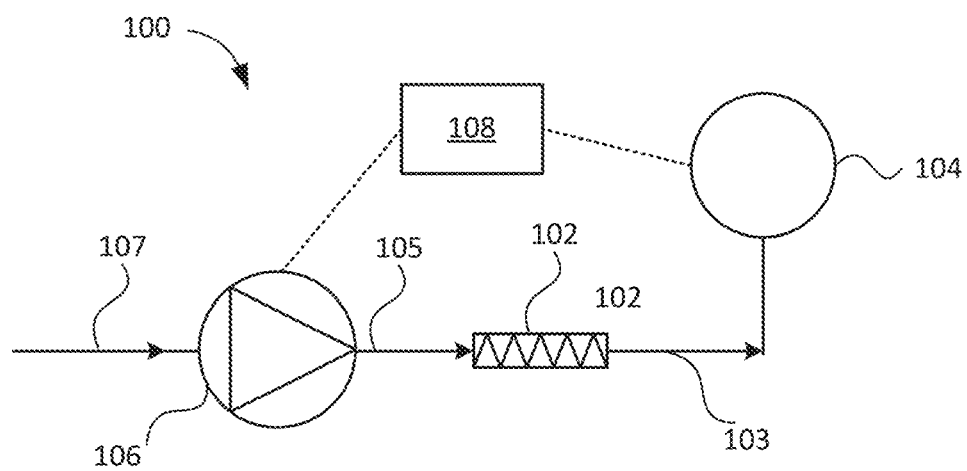
FIG. 1A is a schematic diagram of an example one-scrubber-one-sensor system for analyzing a gas, according to some embodiments.

FIG. 1A is a schematic diagram of an example system 100 for analyzing a gas, according to some embodiments. The system 100 may comprise at least one scrubber and at least one gas sensor. The system 100 in this embodiment comprises a scrubber 102 and a gas sensor 104. The system 100 may therefore also be referred to herein as a "one-scrubber-one-sensor" system.

As used herein, "scrub" or "scrubbing" refers to removing at least one chemical component of the gas and a "scrubber" refers to an apparatus or device that comprises a material capable of scrubbing (the "scrubber material"). The scrubbing may involve one or more physical and/or chemical processes to remove the chemical component(s) from the gas. Physical processes may include adsorption and/or absorption. Chemical processes may include one or more chemical reactions between the chemical component and the scrubber material that convert the chemical component into one or more different chemical entities. Scrubbing may fully or partially remove the chemical component(s) from the gas.

The scrubber material may have selectivity for at least one pre-defined chemical component of the gas. As used herein, "selectivity" or "selective removal" refers to relatively strong physical or chemical interaction with the pre-defined chemical compound(s) and relatively weak interaction (or no interaction) with any other components of the gas. In some embodiments, the scrubber material has selectivity for at least one sulfur compound.

The scrubber material may be a non-aqueous material. As used herein "non-aqueous" refers to a material that is substantially free of water, although it may contain trace amounts of water as an impurity. In some embodiments, the scrubber material may also be substantially free of other solvents, carriers, and the like. In some embodiments, the scrubber material comprises a substantially pure chemical compound. As used herein, "purity" refers to the amount of a chemical compound in a given substance and a "substantially pure" chemical compound refers to a substance in which at least about 50% of the total composition of the substance is the compound of interest. In some embodiments, the purity of the chemical compound of the scrubber material is at least about 60%, at least about 70%, at least about 80%, at least about 90%, at least about 95%, at least about 98%, or at least about 99%. In some embodiments, the scrubber material may be a single substantially pure chemical compound or a mixture of two or more substantially pure chemical compounds. In other embodiments, the scrubber material may have a lower purity if none of the other components interfere with the interaction between the scrubber material and the sulfur compounds in the gas being analyzed.

In some embodiments, the scrubber material is a solid material that selectively removes at least one chemical component of the gas (a "solid-phase scrubber material"). The solid-phase scrubber material may be in the form of powder, pellets, or any other suitable solid form.

In some embodiments, the solid-phase scrubber material comprises a solid form of a carbonate salt, a bicarbonate salt, a metal oxide, or a combination of one or more carbonate salts, bicarbonate salts, and/or metal oxides. In some embodiments, the carbonate salt, bicarbonate salt, or metal oxide is substantially pure. Non-limiting examples of carbonate and bicarbonate salts include $Na_2CO_3$, $CaCO_3$, $K_2CO_3$, $NaHCO_3$ and $KHCO_3$. Non-limiting examples of metal oxides include CaO and ZnO. The solid-phase scrubber material may selectively remove $H_2S$ from the gas. In some embodiments, $H_2S$ reacts with the scrubber material. Non-limiting examples of possible reactions between $H_2S$ and the scrubber material are provided below:

$$xH_2S+M_2(CO_3)_x=M(HS)_x+M(HCO_3)_x$$

$$xH_2S+2M(HCO_3)_x=M_2S_x+2xH_2O+2xCO_2$$

$$xH_2S+M_2O_x=M_2S_x+xH_2O$$

where M is a metal atom and x is equal to its oxidation number.

In other embodiments, the solid-phase scrubber material comprises a hydroxide-based scrubber material. In some embodiments, the hydroxide-based scrubber material comprises a solid form of an alkali metal hydroxide, an alkaline earth metal hydroxide, or a combination of one or more alkali metal hydroxides and/or one or more alkaline earth metal hydroxides. In some embodiments, the alkali metal hydroxide and/or alkaline earth metal hydroxide is substantially pure. The alkali metal hydroxide may comprise NaOH, LiOH, KOH, RbOH, or CsOH. The alkaline earth metal hydroxide may comprise $Ca(OH)_2$, $Ba(OH)_2$, and $Sr(OH)_2$. The hydroxide-based scrubber material may selectively remove $H_2S$ and mercaptans (e.g., TBM) from the gas. Where the gas to be analyzed comprises natural gas, the scrubber material may also remove other mercaptans that are naturally present in the natural gas. In some embodiments, $H_2S$ and mercaptans reacts with the scrubber material. Non-limiting examples of possible reactions between $H_2S$ and mercaptans and the scrubber material are provided below:

$$xH_2S+2M(OH)_x=M_2S_x+2xH_2O$$

$$xRSH+M(OH)_x=M(SR)_x+xH_2O$$

where M is an alkali metal atom or alkaline earth metal atom, x is equal to the oxidation number of the metal atom, and R is an alkyl group In other embodiments, the solid-phase scrubber material comprises an iodate-based scrubber material. In some embodiments, the iodate-based scrubber material comprises a solid form of an iodate salt, or a combination of one or more iodate salts and one or more alkali metal hydroxides or alkaline earth metal hydroxides. In some embodiments, the iodate salt is substantially pure. The iodate salt may comprise $NaIO_3$, $KIO_3$, $Ca(IO_3)_2$, or $Mg(IO_3)_2$. The iodate-based scrubber material may selectively remove $H_2S$ and mercaptans (e.g., TBM) from the gas. Where the gas to be analyzed comprises natural gas, the scrubber material may also remove other mercaptans that are naturally present in the gas.

In other embodiments, the solid-phase scrubber material comprises any other suitable solid material that is capable of scrubbing at least one sulfur compound from a gas.

In other embodiments, the scrubber material is a liquid material that selectively removes at least one chemical component of the gas (a "liquid-phase scrubber material"). The liquid-phase scrubber material may comprise an organic, non-aqueous liquid. In some embodiments, the liquid-phase scrubber material comprises an amine or a mixture of two or more amines. In some embodiments, the amine is substantially pure. Non-limiting examples of amines include monoethanolamine (MEA), diethanolamine (DEA), triethanolamine (TEA), methyldiethanolamine (MDEA), and diglycolamine (DGA). The amine-based scrubber material may selectively remove $H_2S$ from the gas. In some embodiments, $H_2S$ reacts with the scrubber material. Non-limiting examples of possible reactions between $H_2S$ and the scrubber material are provided below:

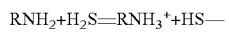

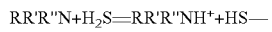

where R, R', and R" are alkyl or alkanol groups.

In embodiments in which the scrubber material is solid-phase, the scrubber 102 may comprise a dry scrubber, a filter, or any other suitable apparatus configured to contain the solid-phase scrubber material. In embodiments in which the scrubber material is liquid-phase, the scrubber 102 may comprise a wet scrubber. The wet scrubber may comprise a bubbler, a spray tower, or any other suitable apparatus configured to contain the liquid-phase scrubber material. As used herein, a "bubbler" refers to any system in which a stream of gas is directed (i.e., "bubbled") through the liquid-phase scrubber material, while a "spray tower" is any system in which the liquid-phase scrubber material is sprayed through or into the gas.

The gas sensor 104 is configured to sense at least one remaining sulfur compound in the gas scrubbed by the scrubber 102. In this embodiment, the gas sensor 104 comprises an electrochemical sensor having one or more electrochemical sensor cells (hereafter also referred to as simply "electrochemical cells"). Electrochemical sensors have several advantages including low cost, low power consumption, and high sensitivity. Electrochemical sensor cells operate by reacting an analyte on the surface of a working electrode, generating an electrical signal that is linearly proportional to the concentration of the analyte. Each sensor cell may comprise a working electrode and a counter electrode (two electrode cell) and optionally a reference electrode (three electrode cell). In some embodiments, the gas sensor 104 comprises two or more electrochemical sensor cells placed in series or parallel with one another.

In other embodiments, the gas sensor 104 comprises a portable gas chromatograph, a UV-Visible spectrophotometer, a stain tube detector, or any other suitable gas sensing device. In alternative embodiments, the gas sensor 104 may be replaced by an individual performing a "sniff" test.

The gas sensor 104 may be in fluid communication with the scrubber 102. In this embodiment, the gas sensor 104 is positioned downstream of the scrubber 102 and fluidly connected to the scrubber 102 by a first fluid conduit 103. As used herein, "fluid conduit" will be understood to include one or more pipes, hoses, ducts, tubes, channels, or the like, in any suitable size, shape, or configuration. Embodiments are not limited to any specific type, number, or structure of fluid conduit.

The system 100 may further comprise a pump 106. The term "pump" in this context refers to any device that moves fluids, including but not limited to pumps, aspirators, etc. The pump 106 may be any suitable type of pump capable of pumping a gas stream. In this embodiment, the pump 106 is positioned upstream of the scrubber 102 and is fluidly connected to the scrubber 102 by a second fluid conduit 105.

In operation, the pump 106 receives a gas stream via an inlet 107 and pumps the gas stream through the second fluid conduit 105 to the scrubber 102. As the gas stream passes through the scrubber 102, one or more sulfur compounds are removed from the gas. The gas sensor 104 then receives a stream of scrubbed gas via the first fluid conduit 103 and the gas sensor 104 senses one or more of the remaining sulfur compounds in the scrubbed gas. In this embodiment, the electrochemical cell of the gas sensor 104 outputs an electrical signal linearly proportional to the concentration of the one or more remaining sulfur compounds.

Figure 1B:
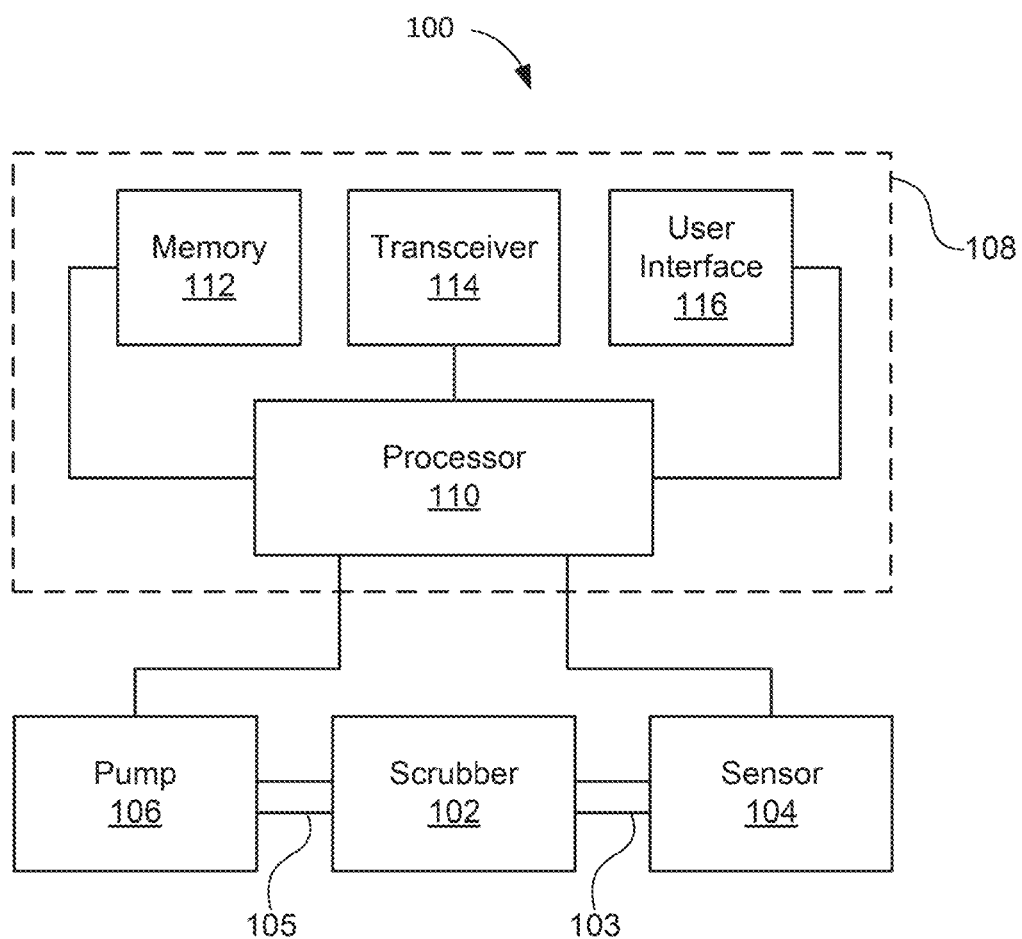
FIG. 1B is a functional block diagram of the system of FIG. 1A.

In some embodiments, the system 100 further comprises a control module 108. The control module may be operatively connected to one or both of the pump 106 and the sensor 104. As shown in FIG. 1B, the control system 108 may comprise at least one processor 110, a memory 112, a transceiver 114, and a user interface 116.

The processor 110 is operatively connected to the memory 112, the transceiver 114, and the user interface 116. The memory 112 stores processor-executable instructions therein that, when executed, cause the processor 110 to implement one or more methods described herein.

The transceiver 114 may be configured to send and receive communications over a communication network such as the Internet. The communication network may be a wired or wireless network. In some embodiments, the transceiver 114 comprises both a transmitter and receiver sharing common circuitry. In other embodiments, the transceiver 114 comprises a separate transmitter and receiver.

In some embodiments, the control module 108 is in communication with one or more remote devices via the communication network. The remote device may comprise, for example, a client computer or server. In some embodiments, the remote device comprises a mobile communications device such as a smartphone or tablet.

The user interface 116 may be configured to display information to a user and/or to receive user input. In some embodiments, the user interface 116 comprises at least one output component and at least one input component. The output component may comprise, for example, at least one of a display screen, a display panel, one or more lights, an audio output device, etc. The input component may comprise, for example, one or more buttons, a touchscreen, keyboard, keypad, trackpad, mouse, microphone, etc.

The processor 110 may be operatively connected to the sensor 104 and may be configured to receive and process sensor output therefrom. For example, the processor 110 may calculate the concentration of one or more sulfur compounds based on the electrical signal generated by the sensor 104. The calculated concentration(s) may be displayed to the user via the user interface 116 and/or may be transmitted to a remote device via the communication network.

The processor 110 may also be operatively connected to the pump 106, for example, via the pump's power source (not shown). The processor 110 may run a program stored in the memory 112 to control the operation of the pump 106. Alternatively, or additionally, the processor 110 may receive user input via the user interface 116 to start, stop, or adjust the operation of the pump 106. In some embodiments, the processor 110 is operable to receive input via a remote device via the communications network. In other embodiments, the pump 106 may be operated manually and the connection between the processor 110 and the pump 106 may be omitted.

In some embodiments, the system 100 further comprises one or more additional components. For example, one or more valves (not shown) may be provided in fluid communication with one or more of the fluid conduits 103, 105, 107 to control the flow of fluid therethrough. In some embodiments, the processor 110 of the control module 108 is operatively connected to the valve(s) to control their operation.

In embodiments in which the gas sensor 104 comprises an electrochemical sensor cell, the system 100 may further comprise an air pump (not shown) and an air purging line (not shown) upstream and in fluid communication with the gas sensor 104. Although electrochemical sensor cells operate normally in hydrocarbon gas (generally a low-humidity and low-oxygen environment) for a short period of time (several minutes to hours), maintaining the cells in a humid (e.g., approximately 10-90% relative humidity) and oxygen-rich environment may improve performance. In these embodiments, ambient air may be pumped through the gas sensor 104, via the air pump and air purging line, to purge the gas sensor 104 between readings and thereby maintain a suitable humid and oxygen-rich environment. Optionally, the system 100 may further comprise a humidity and temperature sensor (not shown) to monitor the gas flowing into or out of the gas sensor 104. In other embodiments, where the gas sensor 104 comprises a different type of sensor (e.g., a portable gas chromatograph, a UV-Visible spectrophotometer, or a stain tube detector), the air pump, air purging line, exhaust line, and humidity and temperature sensor may be omitted.

In some embodiments, the system 100 comprises a single housing (not shown) that encloses all of the components described above. In other embodiments, the system 100 may comprise two or more separate housings, each housing enclosing one or more individual components.

Figure 2:
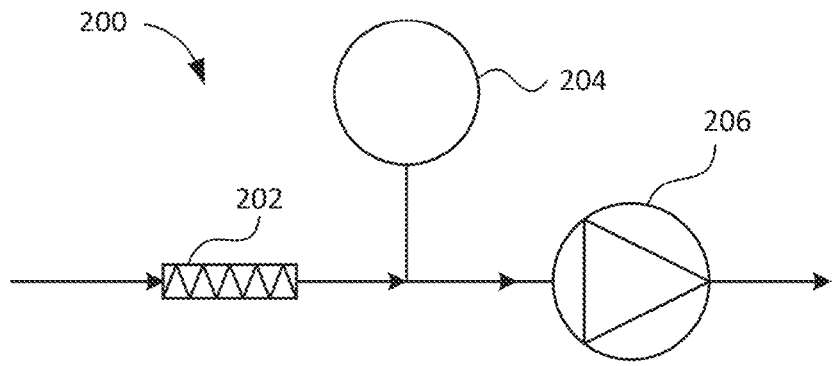
FIG. 2 is a schematic diagram of another example one-scrubber-one-sensor system for analyzing a gas, according to some embodiments.

FIG. 2 is a schematic diagram of another example system 200 for analyzing the gas. The system 200 is an alternative embodiment of a one-scrubber-one-sensor system. As shown in FIG. 2, the system 200 comprises a scrubber 202, a gas sensor 204, and a pump 206. In this embodiment, the gas sensor 204 is positioned downstream of the scrubber 202 and the pump 206 is positioned downstream of the gas sensor 204.

Figure 3:
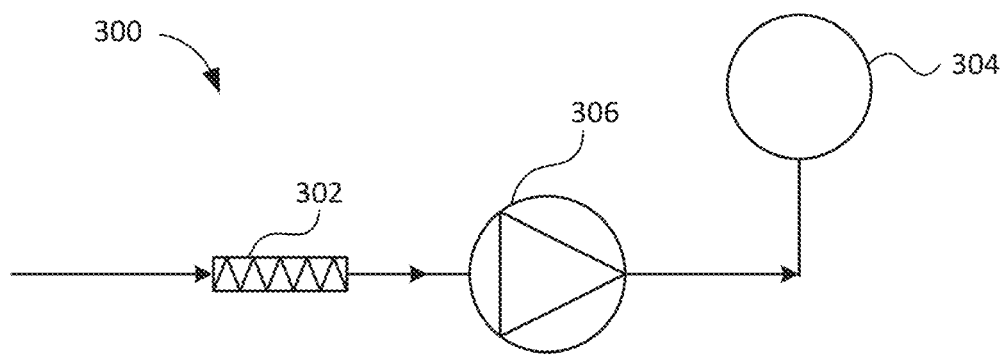
FIG. 3 is a schematic diagram of another example one-scrubber-one-sensor system for analyzing a gas, according to some embodiments.

FIG. 3 is a schematic diagram of another example system 300 for analyzing a gas. The system 300 is another alternative embodiment of a one-scrubber-one-sensor system. As shown in FIG. 3, the system 300 comprises a scrubber 302, a gas sensor 304, and a pump 306. In this embodiment, the pump 306 is positioned between the scrubber 302 and the gas sensor 304.

The system 200 and 300 may each further comprise a control module (not shown) similar to the control module 108 of the system 100 of FIGS. 1A and 1B. The systems 200 and 300 may also comprise any of the other optional components of the system 100 as described above.

Figure 4:
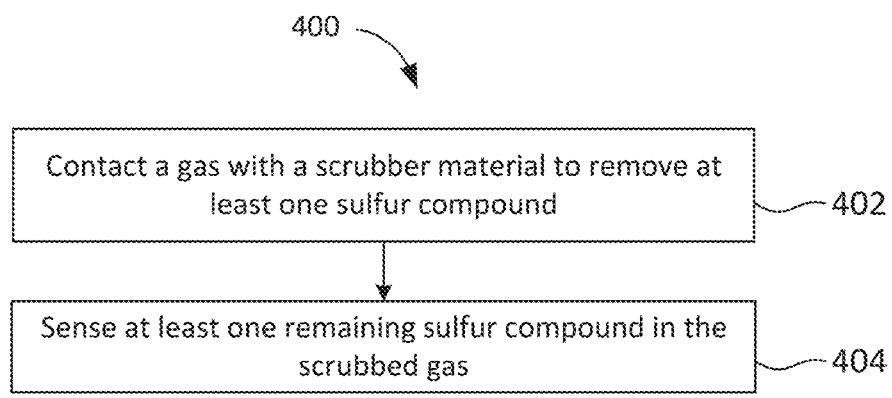
FIG. 4 is a flowchart of an example method for analyzing a gas, according to some embodiments.

FIG. 4 is a flowchart of an example method 400 for analyzing a gas, according to some embodiments, that may be implemented using the systems 100, 200, and 300 of FIGS. 1A-1B, 2, and 3. The method 400 may be used to analyze a gas containing one odorant such as, for example, THT, TBM, MES, NPM, IPM, DMS, SBM, DES, or EM.

At block 402, a gas is contacted with a scrubber material. The term "contact" in this context is intended to include any means by which the gas is brought into contact with the scrubber material. For example, in embodiments in which the scrubber material is solid-phase, the gas may be flowed through the scrubber material. In embodiments in which the scrubber material is liquid phase, the gas may be bubbled through the scrubber material, or the scrubber material may be sprayed into or through the gas. As discussed above, at least one sulfur compound in the gas may react with the scrubber material. In some embodiments, the reaction is instantaneous or near instantaneous such that there is little to no retention time of the gas in the scrubber material.

Contacting the gas with the scrubber material scrubs the gas to remove at least one sulfur compound and thereby produce a scrubbed gas. The gas may be contacted with the scrubber material in the scrubber 102, 202, or 302 of the system 100, 200, or 300 described above. In some embodiments, at least one sulfur compound is completely removed from the gas by the scrubber material such that the compound(s) are no longer present in the scrubbed gas. In other embodiments, at least one sulfur compound is partially removed from the gas such that the concentration of the compound(s) in the scrubbed gas is significantly reduced but small quantities may still be present.

In some embodiments, the scrubber material comprises at least one of a carbonate salt, a bicarbonate salt, a metal oxide, and an amine. In these embodiments, the scrubbing (or "pre-treatment") step removes $H_2S$ from the gas. In other embodiments, the scrubber material comprises at least one of an alkali metal hydroxide, an alkaline earth metal hydroxide, and an iodate salt. In these embodiments, the scrubbing step removes $H_2S$ and one or more mercaptans (e.g., TBM). Where the gas to be analyzed comprises natural gas, the scrubbing step may also remove one or more native mercaptans that are naturally present in the natural gas.

The scrubbing step at block 402 may be performed under any suitable conditions. In embodiments in which the scrubber material is one of the solid-phase scrubber materials, the scrubbing step may be performed at any ambient temperature, including a wide range of temperatures in the field such as between about −50° C. and about 50° C. In embodiments in which the scrubber material is a liquid-phase material, the scrubbing step may be performed at suitable temperature to maintain the viscosity of the liquid. For example, a scrubbing step with an amine-based scrubbing material may be performed at about 0° C. or higher.

At block 404, at least one remaining sulfur compound in the scrubbed gas is sensed. As used herein, "sensing" refers to detecting, measuring, or otherwise acquiring data or information related to at least one sulfur compound in the gas. The sulfur compound(s) may be sensed using any embodiment of the sensors 104, 204, or 304 described above. In some embodiments, the sulfur compound(s) are sensed by an electrochemical sensor that generates an electrical signal, which is linearly proportional to the concentration of the sulfur compound(s).

In some embodiments, the method 400 further comprises calculating a concentration of at least one sulfur compound based on a sensor output. In embodiments in which the sensor is an electrochemical sensor, the sensor output is an electrical signal (I), and the concentration of the sulfur compound can be calculated by dividing the signal by a linear coefficient as shown in Equation 1:

$$C=I/a \quad \text{(Eq. 1)}$$

where a is the linear coefficient.

The concentration may be expressed in ppm or any other suitable unit. In some embodiments, the calculation step is performed by the processor 110 of the control module 108 (or similar control modules of the systems 200 or 300). In other embodiments, the sensor output is transmitted to an external device to perform the calculation or to display the sensor output to a user to perform the calculation manually.

As one specific example of the implementation of the method 400, the gas to be analyzed is natural gas containing TBM as an odorant along with native $H_2S$. At block 402, the scrubber material comprises at least one of a carbonate salt, a bicarbonate salt, a metal oxide, and an amine, and the scrubbing step removes $H_2S$ from the gas. At block 404, the TBM in the gas is sensed by an electrochemical sensor and the sensor output is used to determine the concentration of TBM in the gas. THT, MES, NPM, IPM, DMS, SBM, DES, or EM can also be analyzed in a similar manner.

As another example, the gas to be analyzed is natural gas containing THT as an odorant along with native $H_2S$ and one or more mercaptans. At block 402, the scrubber material comprises at least one of an alkali metal hydroxide, an alkaline earth metal hydroxide, and an iodate salt, and the scrubbing step removes $H_2S$ and one or more mercaptans. At block 404, the THT in the gas is sensed by an electrochemical sensor and the sensor output is used to determine the concentration of THT in the gas. MES, DES, and DMS can also be analyzed in a similar manner.

Figure 5:
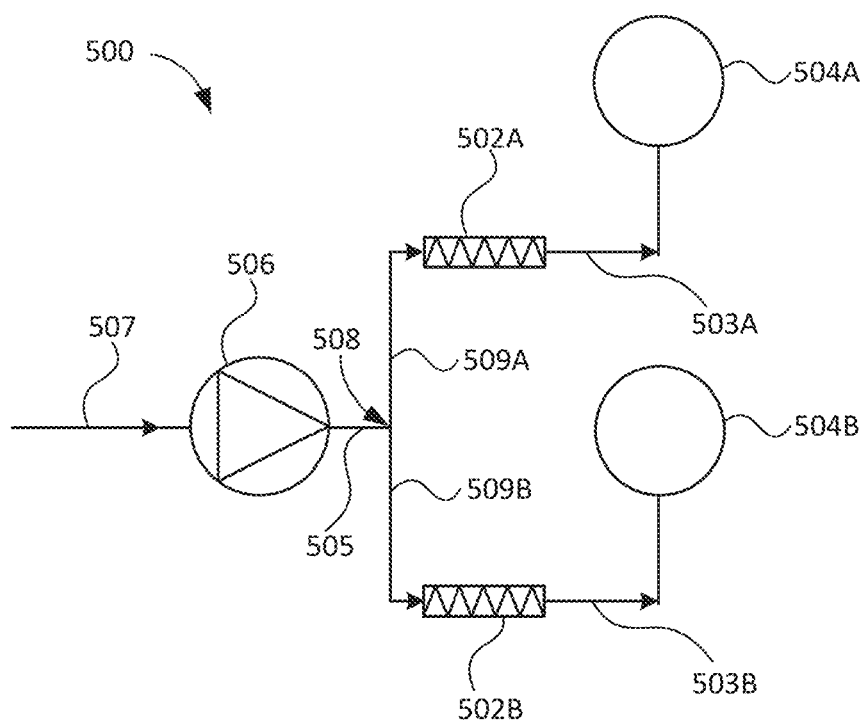
FIG. 5 is a schematic diagram of an example two-scrubber-two-sensor system for analyzing a gas, according to some embodiments.

FIG. 5 is a schematic diagram of another example system 500 for analyzing a gas, according to some embodiments. The system 500 in this embodiment comprises a first scrubber 502A, a second scrubber 502B, a first gas sensor 504A, and a second gas sensor 504B. The system 500 may therefore be referred to herein as a "two-scrubber-two-sensor" system.

The first scrubber 502A may comprise a first scrubber material and the second scrubber 502B may comprise a second scrubber material. In this embodiment, the first scrubber material comprises at least one of a carbonate salt, a bicarbonate salt, a metal oxide, and an amine, and the second scrubber material comprises at least one of an alkali metal hydroxide, an alkaline earth metal hydroxide, and an iodate salt.

In this embodiment, the first and second sensors 504A and 504B each comprise an electrochemical sensor comprising one or more electrochemical cells. In other embodiments, the first and second sensors 504A and 504B comprise any other suitable type of sensor including any of the sensors described above for the sensor 104 of the system 100. The first and second sensors 504A and 504B may be the same type of sensor or different types of sensors.

The first sensor 504A may be in fluid communication with the first scrubber 502A and the second sensor 504B may be in fluid communication with the second scrubber 502B. In this embodiment, the first sensor 504A is downstream of the first scrubber 502A and is fluidly connected to the first scrubber 502A by a first fluid conduit 503A. The second sensor 504B is downstream of the second scrubber 502B and fluidly connected to the second scrubber 502B by a second fluid conduit 503B.

The system 500 may further comprise at least one pump. In this embodiment, the system 500 comprises a pump 506 upstream of both the first and second scrubbers 502A and 502B. The pump 506 may be fluidly connected to the first and second scrubbers 502A and 502B via a branched fluid conduit 505. The fluid conduit 505 may comprise a junction 508 that splits the fluid conduit 505 into a first branch 509A and a second branch 509B. The first branch 509A may fluidly connect to the first scrubber 502A and the second branch 509B may fluidly connect to the second scrubber 502B.

The system 500 may operate as follows. The pump 506 receives a gas stream via an inlet 507 and pumps the gas stream through the branched fluid conduit 505, where it is split at the junction 508 into a first gas stream and a second gas stream. The first gas stream flows through the first branch 509A to the first scrubber 502A and the second gas stream flows through the second branch 509B to the second scrubber 502B.

As the first gas stream passes through the first scrubber 502A, one or more sulfur compounds are removed from the gas to produce a first scrubbed gas. The first scrubbed gas is received by the first gas sensor 504A via the first fluid conduit 503A and the first gas sensor 504A senses one or more of the remaining sulfur compounds in the first scrubbed gas. In this embodiment, the electrochemical cell of the first gas sensor 504A outputs an electrical signal linearly proportional to the concentration of the one or more remaining sulfur compounds.

As the second gas stream passes through the second scrubber 502B, one or more sulfur compounds are removed from the gas to produce a second scrubbed gas. The second scrubbed gas is received by the second gas sensor 504B via the second fluid conduit 503B and the second gas sensor 504B senses one or more of the remaining sulfur compounds in the second scrubbed gas. In this embodiment, the electrochemical cell of the second gas sensor 504B outputs an electrical signal linearly proportional to the concentration of the one or more remaining sulfur compounds.

The system 500 may comprise a control module (not shown) similar to the control module 108 of the system 100 of FIG. 1B. In some embodiments, where at least one of the gas sensors 504A and 504B comprises an electrochemical sensor cell, the system 500 may comprise an air pump, air purging line, exhaust line and, optionally, a humidity and temperature sensor (all not shown) as described above with respect to the system 100.

Figure 6A:
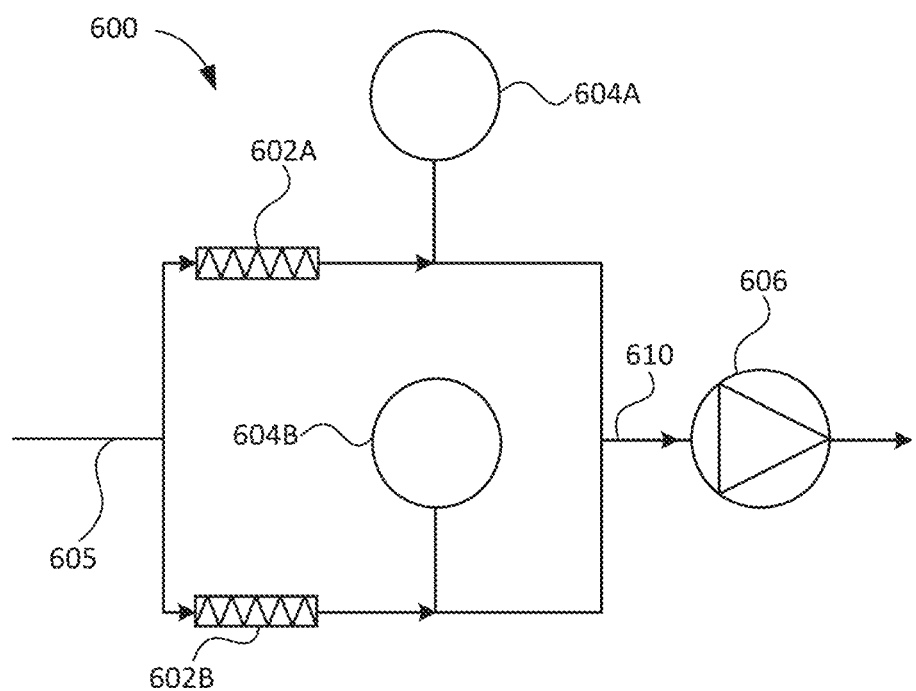
FIG. 6A is a schematic diagram of another example two-scrubber-two-sensor system for analyzing a gas, according to some embodiments.

FIGS. 6A, 6B, 6C, and 6D are schematic diagrams of additional example systems 600, 620, 630, and 640, respectively, for analyzing the gas. The systems 600, 620, 630, and 640 are alternative embodiments of two-scrubber-two-sensor systems As shown in FIG. 6A, the system 600 comprises a first scrubber 602A and a second scrubber 602B, a first gas sensor 604A and a second gas sensor 604B, and a pump 606. The first and second scrubbers 602A and 602B and the first and second gas sensors 604A and 604B may be similar to the first and second scrubbers 502A and 502B and the first and second gas sensors 504A and 504B, respectively, of the system 500 as described above. A first branched conduit 605 may be fluidly connected to the first scrubber 602A and the second scrubber 602B.

In this embodiment, the pump 606 is positioned downstream of the first and second gas sensors 604A and 604B. The pump 606 is fluidly connected to the first and second gas sensors 604A and 604B by a second branched conduit 610.

The system 600 may operate in a similar manner to the system 500 as described above. Briefly, the gas may be received by the first branched fluid conduit 605 and split into a first fluid stream and a second fluid stream. The pump 606 may draw the first gas stream through the first scrubber 602A to the first gas sensor 604A and draw the second gas stream through the second scrubber 602B to the second gas sensor 604B. The first and second scrubbed gas streams may be combined downstream of the first and second gas sensors 604A and 604B in the second branched conduit 610, from which they are pumped out of the system 600.

Figure 6B:
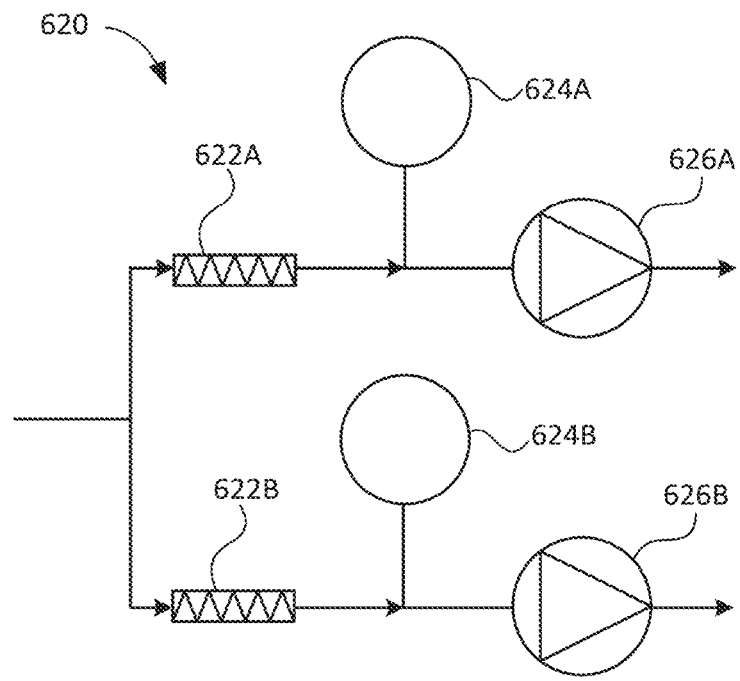
FIG. 6B is a schematic diagram of another example two-scrubber-two-sensor system for analyzing a gas, according to some embodiments.

As shown in FIG. 6B, the system 620 comprises a first scrubber 622A, a second scrubber 622B, a first sensor 624A, and a second sensor 624B. In this embodiment, the system 620 further comprises a first pump 626A and a second pump 626B. The first pump 626A is positioned downstream of the first sensor 624A and the second pump 626B is positioned downstream of the second sensor 624B.

Figure 6C:
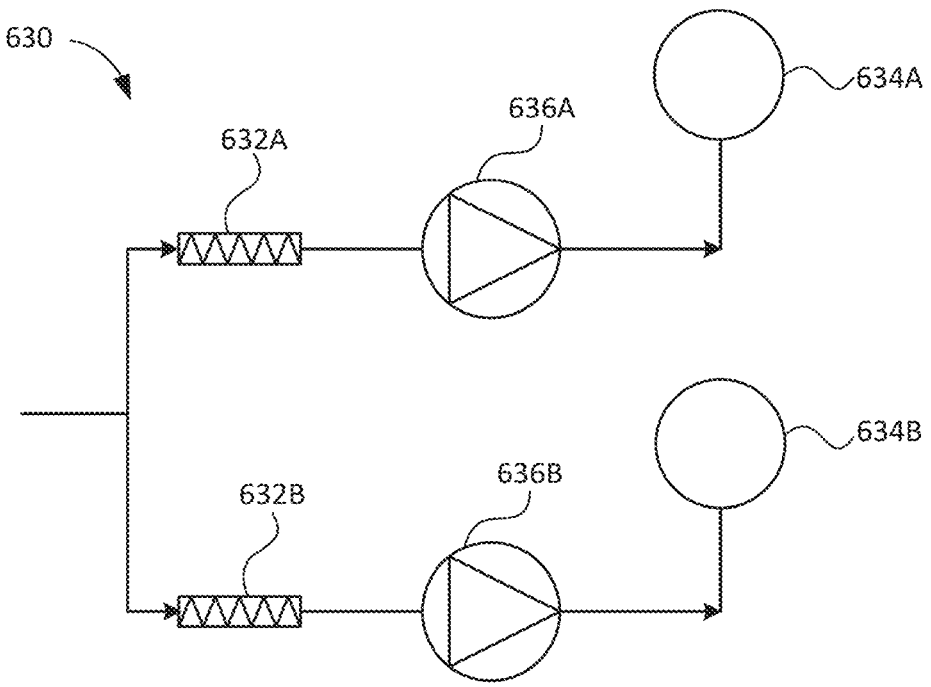
FIG. 6C is a schematic diagram of another example two-scrubber-two-sensor system for analyzing a gas, according to some embodiments.

As shown in FIG. 6C, the system 630 comprises a first scrubber 632A, a second scrubber 632B, a first sensor 634A, a second sensor 634B, a first pump 636A, and a second pump 636B. In this embodiment, the first pump 636A is positioned between the first scrubber 632A and the first sensor 634A and the second pump 636B is positioned between the second scrubber 632B and the second sensor 634B.

Figure 6D:
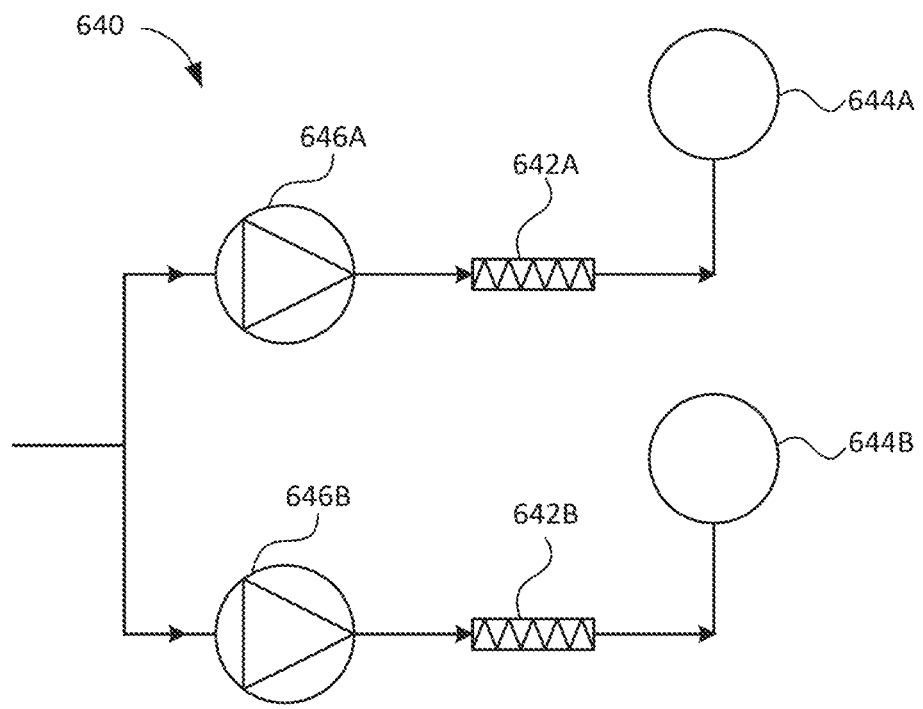
FIG. 6D is a schematic diagram of another example two-scrubber-two-sensor system for analyzing a gas, according to some embodiments.

As shown in FIG. 6D, the system 640 comprises a first scrubber 642A, a second scrubber 642B, a first sensor 644A, a second sensor 644B, a first pump 646A, and a second pump 646B. The first pump 646A is positioned upstream of the first scrubber 642A and the second pump 646B is positioned upstream of the second scrubber 642B.

The systems 620, 630, and 640 may otherwise operate in a similar manner to the systems 500 and 600 as described above.

Figure 7:
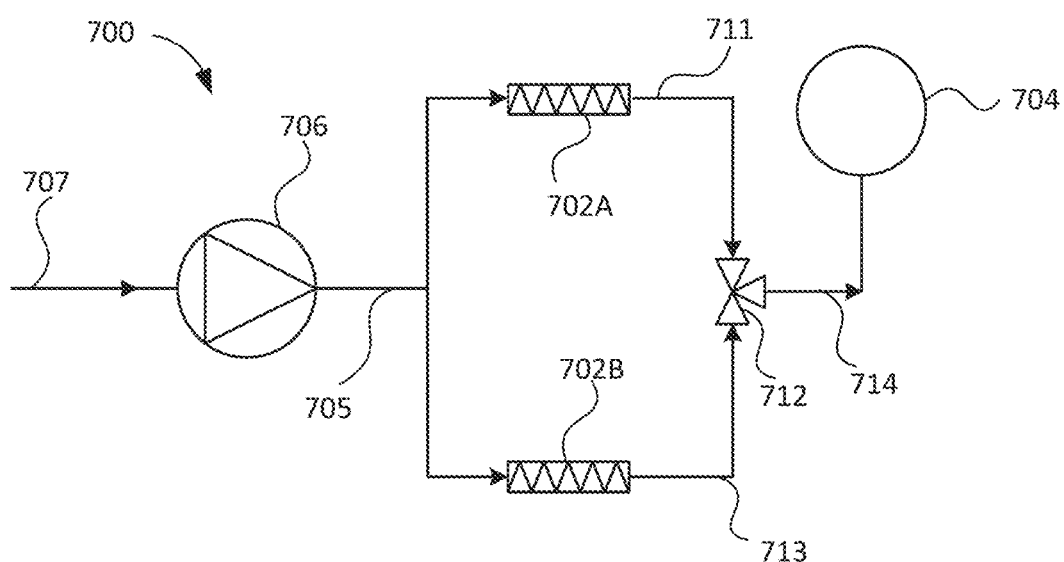
FIG. 7 is a schematic diagram of an example two-scrubber-one-sensor system for analyzing a gas, according to some embodiments.

FIG. 7 is a schematic diagram of another example system 700 for analyzing a gas. The system 700 in this embodiment comprises a first scrubber 702A, a second scrubber 702B, a gas sensor 704, and a pump 706. The system 700 may also be referred to herein as a "two-scrubber-one-sensor" system. The system 700 is a simplified embodiment of the two-scrubber-two-sensor systems described above.

The first and second scrubbers 702A and 702B may be similar to the first and second scrubbers 502A and 502B, respectively, of the system 500 as described above. In this embodiment, the pump 706 is upstream of the first and second scrubbers 702A and 702B and is fluidly connected to the first and second scrubbers 702A and 702B via a branched fluid conduit 705.

The system 700 in this embodiment further comprises a three-way valve 712. The valve 712 is in fluid communication with the first and second scrubbers 702A and 702B and the gas sensor 704 and is positioned downstream of the first and second scrubbers 702A and 702B and upstream of the gas sensor 704. The valve 712 in this embodiment is fluidly connected to the first scrubber 702A via a first fluid conduit 711, to the second scrubber 702B via a second fluid conduit 713, and to the gas sensor 704 via a third fluid conduit 714.

The system 700 may operate as follows. The pump 706 receives a gas stream via an inlet 707 and pumps the gas stream through the branched fluid conduit 705 where it is split into a first gas stream and a second gas stream. The first gas stream flows through the first scrubber 702A and the second gas stream flows through the second scrubber 702B. A first scrubbed gas flows through the first fluid conduit 711 and a second scrubbed gas flows through the second fluid conduit 713.

The valve 712 may be selectively movable between a first position and a second position. When the valve 712 is in the first position, the first fluid conduit 711 is in fluid communication with the third fluid conduit 714 and the gas sensor 704 receives the first scrubbed gas. When the valve 712 is in the second position, the second fluid conduit 713 is in fluid communication with the third fluid conduit 714 and the gas sensor 704 receives the second scrubbed gas. Thus, the gas sensor 704 may alternate between sensing one or more sulfur compounds in the first scrubbed gas and one or more sulfur compounds in the second scrubbed gas.

Alternatively, instead of a three-way valve 712, the system 700 can comprise two one-way valves (not shown). A first one-way valve may be in fluid communication with the first fluid conduit 711 to control the flow of the first scrubbed gas and a second one-way valve may be in fluid communication with the second fluid conduit 713 to control the flow of the second scrubbed gas. In other embodiments, the three-way valve 712 (or two one-way valves) may be positioned upstream of the first and second scrubbers 702A and 702B to alternate the flow of gas into the first scrubber 702A and the second scrubber 702B, thereby alternating the generation of the first gas stream and the second gas stream.

The system 700 may further comprise a control module (not shown) similar to the control module 108 of the system 100 of FIG. 1B. The control module may be operatively connected to the three-way valve, or two one-way valves, to control operation thereof.

Figure 8:
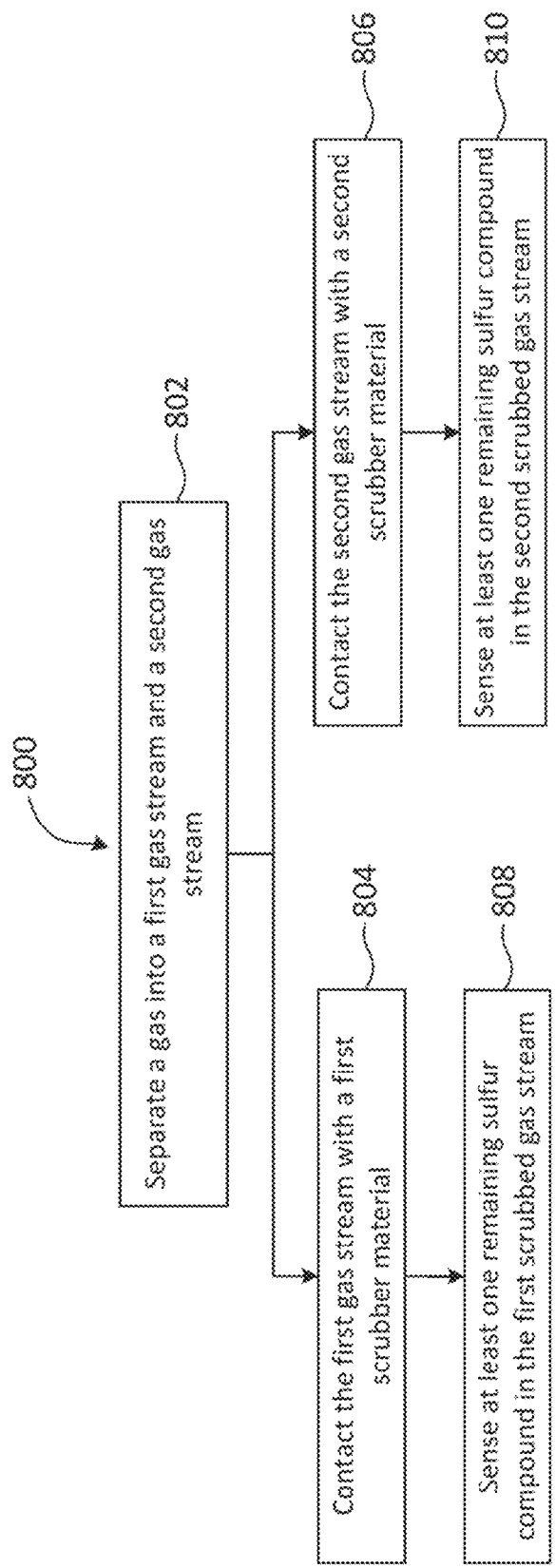
FIG. 8 is a flowchart of another example method for analyzing a gas, according to some embodiments.

FIG. 8 is a flowchart of an example method 800 for analyzing a gas, according to some embodiments. The method 800 may be implemented by embodiments of the systems 500, 600, 620, 630, 640, and 700 of FIGS. 5, 6A, 6B, 6C, 6D and 7, respectively. For simplicity, only systems 500, 600, and 700 will be referred to in the description of the method 800 below. The method 800 will be described using natural gas as the gas to be analyzed, wherein the natural gas contains two odorants (TBM and MES) along with native $H_2S$ and mercaptans. However, it will be understood that the method 800 may be adapted to analyze any other gases comprising two or more odorants such as sulfur compounds.

At block 802, the gas is separated into a first gas stream and a second gas stream. In some embodiments, the gas is separated by pumping the gas through a branched fluid conduit such as the branched fluid conduit 505, 605, or 705 of the system 500, 600, or 700.

At block 804, the first gas stream is contacted with a first scrubber material. Contacting the first gas stream with the first scrubber material scrubs the gas to remove at least one sulfur compound and thereby produce a first scrubbed gas stream. The first gas stream may be contacted with the first scrubber material by the first scrubber 502A, 602A, or 702A of the system 500, 600, or 700. In this embodiment, the first scrubber material comprises at least one of a carbonate salt, a bicarbonate salt, a metal oxide, and an amine, and the scrubbing step removes $H_2S$ from the first gas stream.

At block 806, a second gas stream is contacted with a second scrubber material. Contacting the second gas stream with the second scrubber material scrubs the gas to remove at least one sulfur compound and thereby produce a second scrubbed gas stream. The second gas stream may be scrubbed by the second scrubber 502B, 602B, or 702B of the system 500, 600, or 700. In this embodiment, the second scrubber material comprises at least one of an alkali metal hydroxide, an alkaline earth metal hydroxide, and an iodate salt, and the scrubbing step removes $H_2S$, TBM, and native mercaptans from the second gas stream.

At block 808, at least one remaining sulfur compound in the first scrubbed gas stream is sensed. The sulfur compound(s) may be sensed by the first sensors 504A or 604A of the systems 500 or 600, respectively, or by the sensor 704 of the system 700 when the valve 712 is in the first position. A first sensor output may be generated by the first sensor 504A or 604A or the sensor 704. In this example, both TBM and MES are sensed in the first scrubbed gas stream and the first sensor output is a total electrical signal ($I_A$) induced by TBM and MES.

At block 810, at least one remaining sulfur compound in the second scrubbed gas stream is sensed. The sulfur compound(s) may be sensed by the second sensors 504B or 604B of the systems 500 or 600, respectively, or by the sensor 704 of the system 700 when the valve 712 is in the second position. A second sensor output may be generated by the second sensor 504B or 604B or the sensor 704. In this example, MES is sensed in the second gas stream and the second sensor output is an electrical signal ($I_B$) induced by MES.

In some embodiments, the steps at blocks 804 and 808 are performed approximately simultaneously as the steps of blocks 806 and 810. In other embodiments, the steps at blocks 804 and 808 can be performed before or after the steps of blocks 806 and 810.

The method 800 may further comprise calculating a concentration of at least one sulfur compound based on the first and second sensor output. In this example, the concentrations of TBM ($C_{TBM}$) and MES ($C_{MES}$) can be computed by Equation 2 as follows:

$$C_{MES} = I_B/a$$

$$C_{TBM} = (I_A - I_B)/b \quad \text{(Eq. 2)}$$

where a and b are the linear coefficients.

Thus, the method 800 can be used to determine the concentrations of two different sulfur-based odorants within a hydrocarbon gas. It will be understood that the method 800 may be adapted for other types of gases and other combinations of odorants. For example, the method 800 may be adapted to determine the concentrations of an odorant blend comprising an organic sulfide and a mercaptan (e.g., TBM/MES blends or TBM/THT blends). Embodiments are not limited to the specific odorants described herein.

Figure 9:
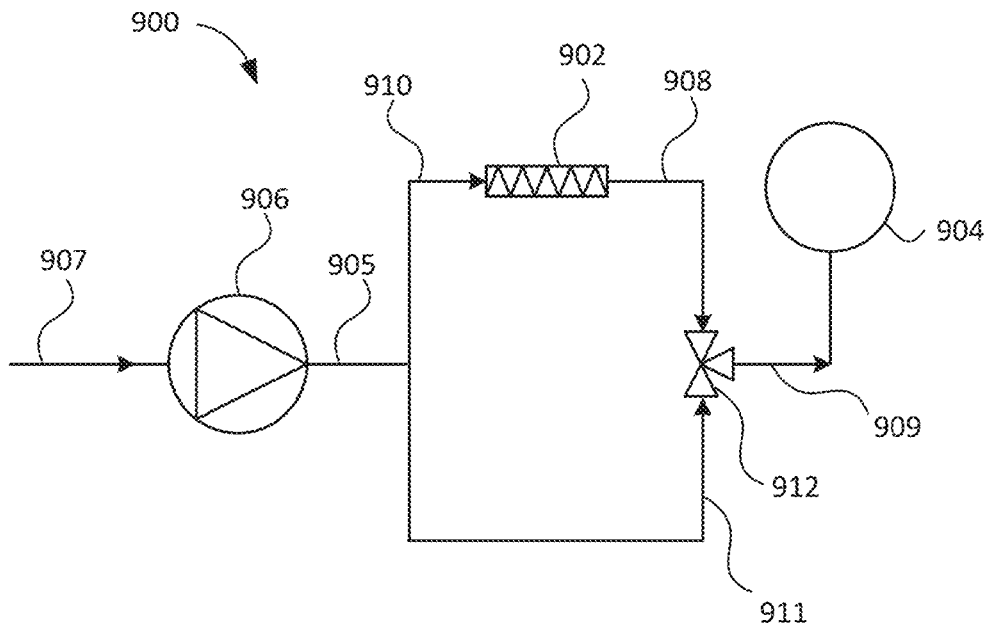
FIG. 9 is a schematic diagram of another example one-scrubber-one-sensor system, according to some embodiments.

FIG. 9 is a schematic diagram of another example system 900 for analyzing a gas, according to some embodiments. The system 900 comprises a scrubber 902, a gas sensor 904, and a pump 906. The system 900 is an alternative embodiment of a one-scrubber-one-sensor system that may be used to determine $H_2S$ content in a hydrocarbon gas.

The scrubber 902 may comprise a scrubber material that selectively removes $H_2S$ from the gas. For example, the scrubber material may comprise at least one of a carbonate salt, a bicarbonate salt, a metal oxide, and an amine. The gas sensor 904 in this embodiment comprises an electrochemical sensor comprising one or more electrochemical cells. In other embodiments, the gas sensor 904 comprises any other suitable type of gas sensor.

The system 900 may further comprise a three-way valve 912 between the scrubber 902 and the sensor 904. The valve 912 may be fluidly connected to the scrubber 902 by a first fluid conduit 908 and fluidly connected to the sensor 904 by a second fluid conduit 909. The system 900 may further comprise a control module (not shown) operatively connected to the three-way valve 912 to control operation thereof.

The pump 906 in this embodiment is positioned upstream of the scrubber 902 and is fluidly connected to the scrubber 902 via a branched fluid conduit 905. The branched fluid conduit 905 may comprise a first branch 910 and a second branch 911. The first branch 910 may be fluidly connected to the scrubber 902 and the second branch 911 may be fluidly connected to the three-way valve 912.

In operation, the pump 906 receives a gas stream via an inlet 907 and pumps the gas stream through the branched fluid conduit 905, where it is split into a first gas stream and a second gas stream. The first gas stream flows through the first branch 910 to the scrubber 902 where it is scrubbed to produce a scrubbed gas stream. The scrubbed gas stream flows through the first fluid conduit 908 to the valve 912. The second gas stream is an "unscrubbed" stream of the gas that flows through the second branch 911 directly to the valve 912.

The valve 912 may have a first position and a second position. When the valve 912 is in the first position, the first fluid conduit 908 is in fluid communication with the second fluid conduit 909 and the gas sensor 904 receives the scrubbed gas stream from the scrubber 902. When the valve 912 is in the second position, the second branch 911 of the branched fluid conduit 905 is in fluid communication with the second fluid conduit 909 and the gas sensor 904 receives the unscrubbed gas stream from the pump 906. Thus, the gas sensor 904 may alternate between sensing total sulfur content of the unscrubbed gas and sensing total sulfur content of the scrubbed gas (from which $H_2S$ has been removed) depending on the position of the valve 912. As described in more detail below with respect to the method 1000, the system 900 may thereby be used to determine the $H_2S$ concentration of the hydrocarbon gas.

In some embodiments, the system 900 may be integrated with one of the systems 100, 200, 300, 500, 600, 700 described above by connecting a fluid conduit for unscrubbed gas to one of the sensors in the system and providing a valve in fluid communication with the fluid conduit to control the flow of unscrubbed gas therethrough.

Figure 10:
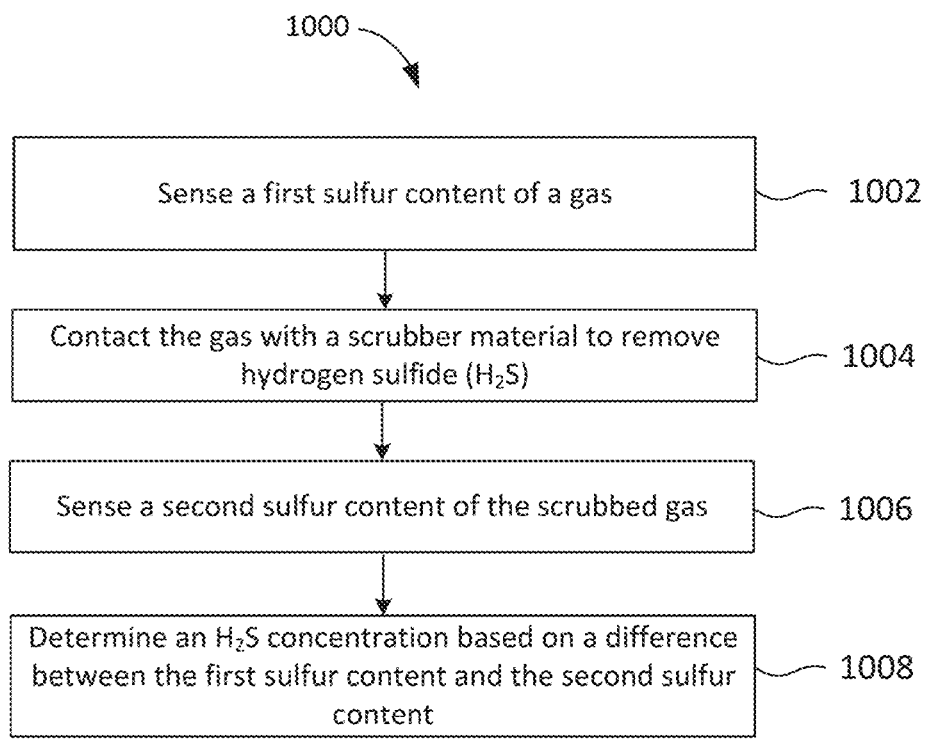
FIG. 10 is a flowchart of another example method for analyzing a gas, according to some embodiments.

FIG. 10 is a flowchart of an example method 1000 for analyzing a gas, according to some embodiments, that may be implemented using the system 900. The method 1000 may be used to analyze $H_2S$ in a hydrocarbon gas.

At block 1002, a first sulfur content of the gas is sensed. As used herein "sulfur content" refers to the total content of sulfur compounds in the gas. The first sulfur content may be sensed by the sensor 904 of the system 900 when the valve 912 is in the second position such that unscrubbed gas is received by the sensor 904. A first sensor output may be generated by the sensor 904. In this example, the first sensor output is a total electrical signal ($I_C$) induced by the sulfur compounds in the unscrubbed gas.

At block 1004, the gas is contacted with a scrubber material. Contacting the gas with the scrubber material scrubs the gas to remove $H_2S$ and thereby produce a scrubbed gas. The gas may be scrubbed through the scrubber 902 with a scrubber material comprising at least one of a carbonate salt, a bicarbonate salt, a metal oxide, and an amine.

At block 1006, a second sulfur content of the scrubbed gas is sensed. The second sulfur content may be sensed by the sensor 904 when the valve 912 is in the first position such that scrubbed gas is received by the sensor 904. A second sensor output may be generated by the sensor 904. In this example, the second sensor output is a total electrical signal ($I_A$) induced by the remaining sulfur compounds in the scrubbed gas.

At block 1008, an $H_2S$ concentration of the gas is determined based on a difference between the first sulfur content and the second sulfur content. The $H_2S$ concentration may be calculated using Equation 3 as follows:

$$C_{H2S} = (I_c - I_A)/c \qquad \text{(Eq. 3)}$$

where c is the linear coefficient of $H_2S$ concentration to the first sensor output.

In some embodiments, the method 1000 may be combined or performed in parallel with the method 400 or 800 described above. Thus, the concentration of $H_2S$ in a gas can be determined along with the concentration of one or more odorants.

Therefore, embodiments of the systems and methods described herein may be used to analyze odorants in a gas with high accuracy and sensitivity, while reducing or eliminating the cross-sensitivity issues of conventional electrochemical sensor-based approaches. Some embodiments of the systems and methods allow the concentrations of individual odorants to be determined in a blend of two or more odorants.

The systems described herein may be relatively inexpensive and may be deployed as automated field sensors in some embodiments. This unmanned approach may also allow for faster sampling (e.g., on a daily or hourly basis) resulting in near real-time analysis of odorants in natural gas pipelines and substations.

Moreover, embodiments of the disclosed systems are compact and require few electronic parts and may therefore be suitable for analyzing odorants in hazardous locations. Further, by using non-aqueous material as the scrubber material, the systems may avoid the need for additional filtration or moisture trapping between the scrubber(s) and the sensors(s), while maintaining performance of the sensor (s). The non-aqueous scrubber materials may also allow the systems to be used in the field across a wide temperature range without risk of freezing the scrubber material and/or requiring the concentration of the scrubber material to be compensated due to evaporation.

Other variations of the systems and methods described herein are also possible. As discussed in the Examples below, when the hydrocarbon gas to be analyzed by the system is already pressurized, alternative embodiments may also be provided in which the pump(s) are omitted, and the system instead comprises a pressure regulator and flow meter. It will also be understood that although particular configurations of the systems 100, 200, 300, 500, 600, 620, 630, 640, 700, and 900 are shown in FIGS. 1A-1B, 2, 3, 5, 6A-6D, 7, and 9 described above, other configurations are possible and embodiments are not limited to the specific configurations provided herein, including the specific number and placement of fluid conduits, valves, etc.

EXAMPLES

Figure 11:
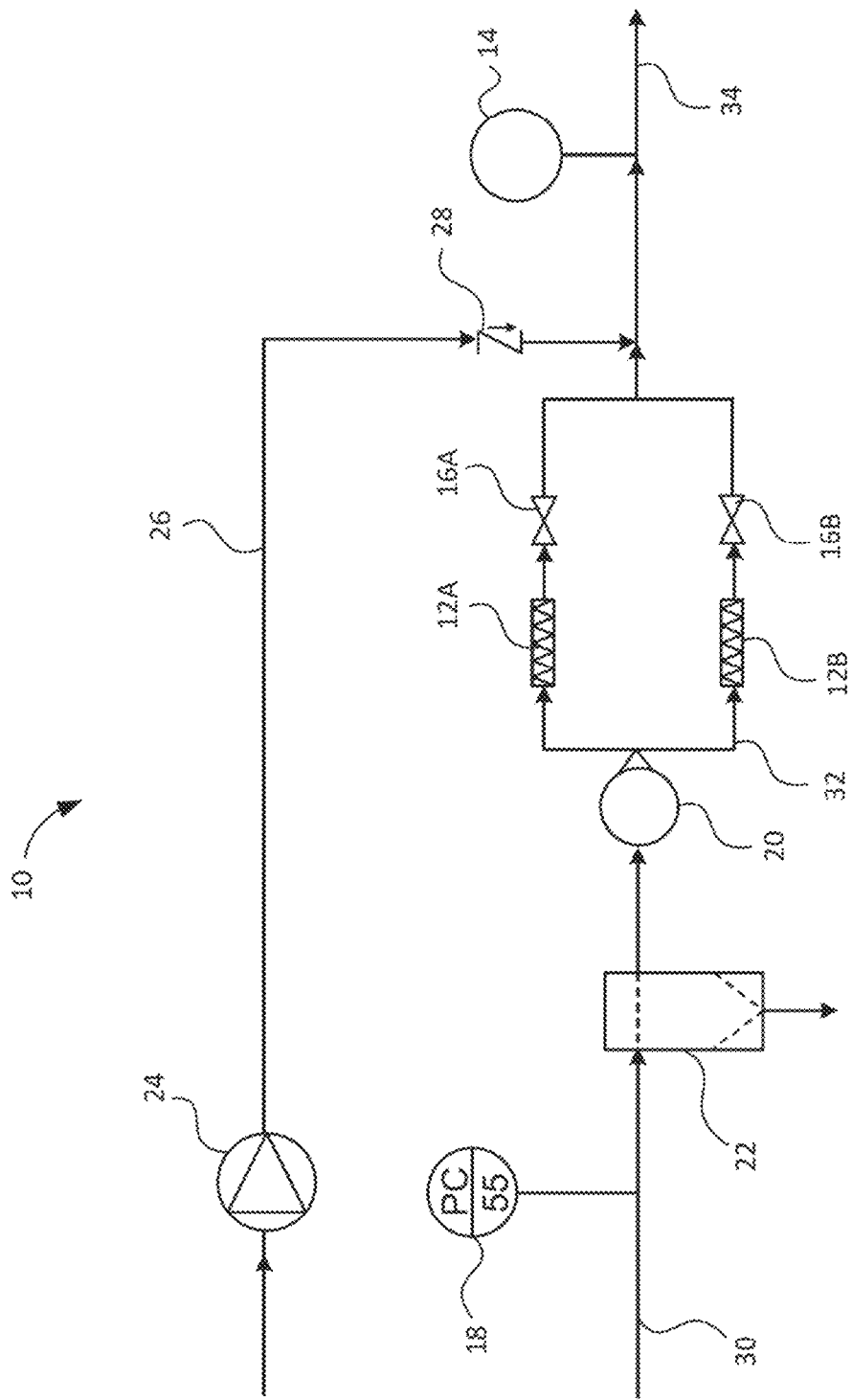
FIG. 11 is a schematic diagram of an experimental system for analyzing a gas.

Experiments were performed using an experimental system 10 as shown in FIG. 11. The experimental system 10 is similar to the system 700 of FIG. 7 with two scrubbers and one electrochemical sensor.

As shown in FIG. 11, the experimental system 10 comprises a first scrubber 12A and a second scrubber 12B in fluid communication with an electrochemical sensor 14. The first scrubber 12A contains $CaCO_3$ or MDEA as a first scrubber material (to remove $H_2S$) and the second scrubber 12B contains a mixture of NaOH and $Ca(OH)_2$ as a second scrubber material (to remove $H_2S$ and mercaptans). A first on/off valve 16A is provided between the first scrubber 12A and the sensor 14 and a second on/off valve 16B is provided between the second scrubber 12B and the sensor 14.

In the experimental system 10, a natural gas sample is drawn from a pressurized pipeline and the sensing tests are performed at ambient pressure. Thus, in the experimental system 10, a combination of a pressure regulator 18 and a flow meter 20 is used instead of a pump. A coalescing filter 22 is provided between the pressure regulator 18 and the flow meter 20.

In addition, the experimental system 10 includes an air pump 24 and an air purging line 26 to purge the electrochemical sensor 14 with ambient air between the sensing tests. A check valve 28 is in fluid communication with the air purging line 26 to control the flow of air therethrough.

In operation, a sample inlet 30 receives a pressurized natural gas stream, which flows through the pressure regulator 18, coalescing filter 22, and flow meter 20 before being split into a first gas stream and a second gas stream via a branched conduit 32. The first gas stream flows through the first scrubber 12A to produce a first scrubbed gas and the second gas stream flows through the second scrubber 12B to produce a second scrubbed gas.

When the first on/off valve 16A is on (i.e., open) and the second on/off valve is off (i.e., closed), the first gas stream will flow to the electrochemical sensor 14 to allow the sensor 14 to sense at least one remaining sulfur compound in the first scrubbed gas. When the first on/off valve 16A is off (i.e., closed) and the second on/off valve is on (i.e., open), the second gas stream will flow to the electrochemical sensor 14 to allow the sensor 14 to sense at least one remaining sulfur compound in the second scrubbed gas. The air pump 24 and the air purging line 26 are used to purge the sensor 14 between readings and the purged air flows out of an exhaust line 34.

Figure 12:
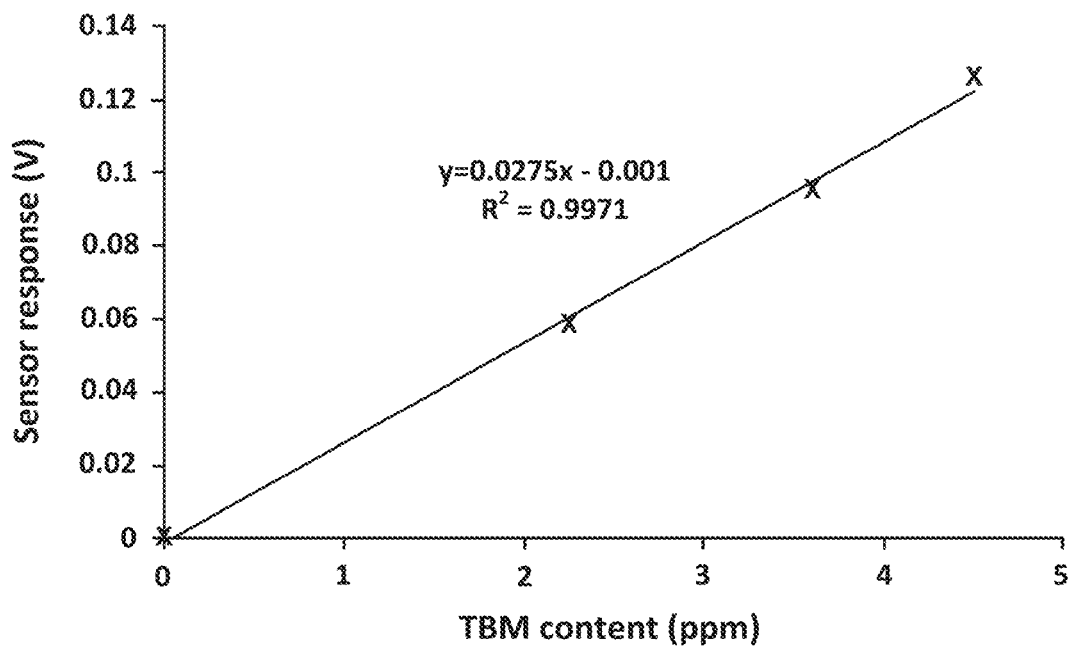
FIG. 12 is a line graph showing electrochemical sensor output in response to varying concentrations of TBM.
Figure 13:
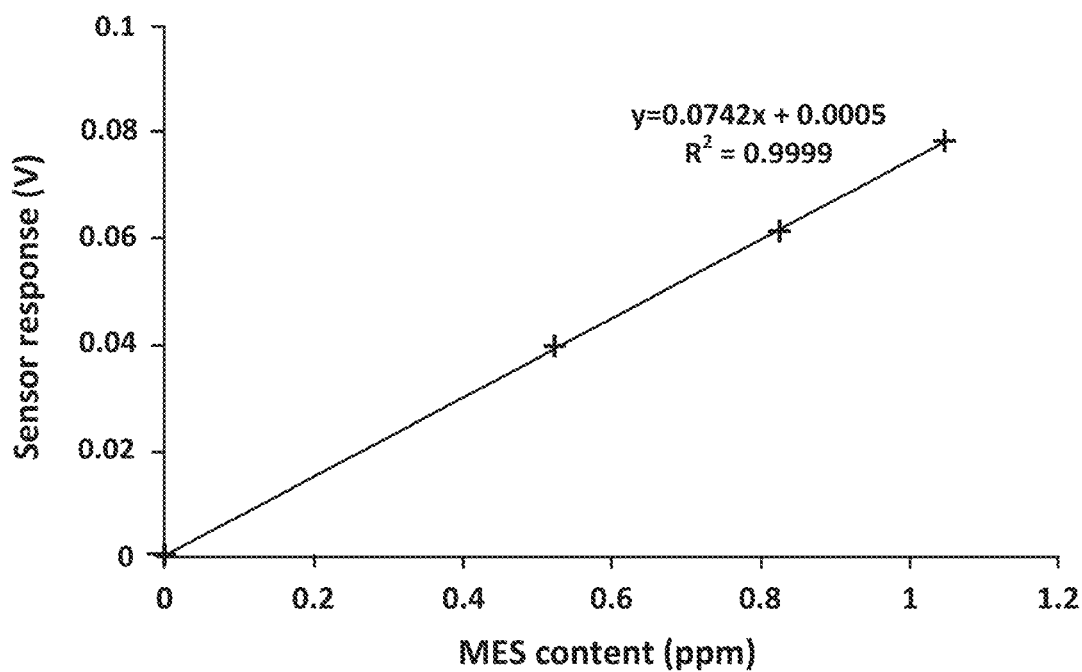
FIG. 13 is a line graph showing electrochemical sensor output in response to varying concentrations of MES.

Gas samples with varying concentrations of TBM and MES were tested using the experimental system. As shown in FIGS. 12 and 13, the voltage signals from the electrochemical sensor are linearly proportional to the concentrations of TBM and MES, respectively.

Figure 14A:
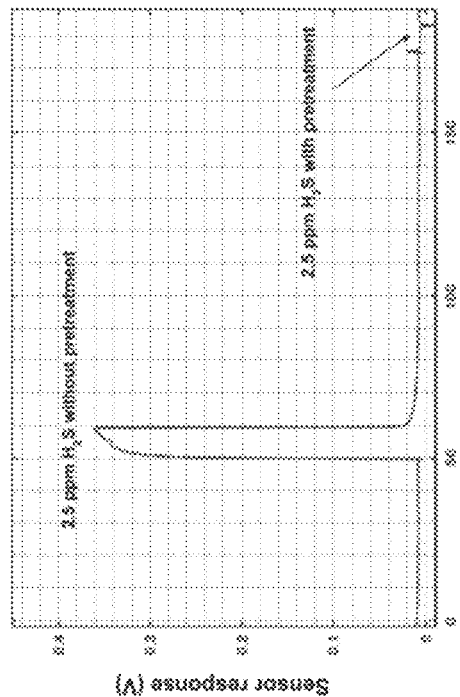
FIG. 14A is a line graph showing electrochemical sensor output in response to TBM, with and without a pre-treatment step with NaOH and $Ca(OH)_2$ scrubber material.
Figure 14B:
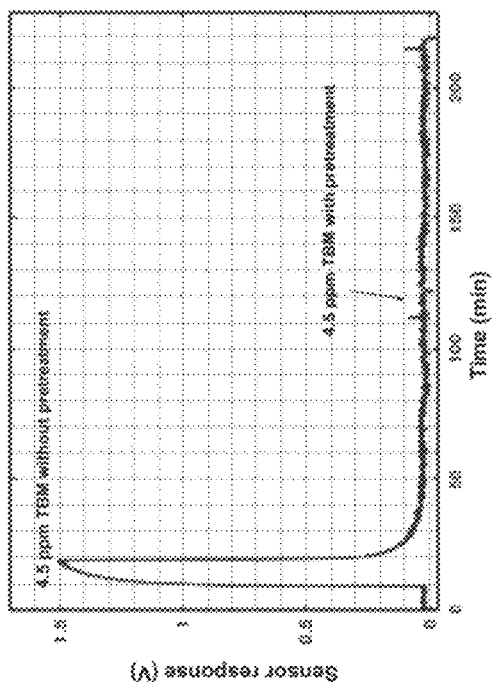
FIG. 14B is a line graph showing electrochemical sensor output in response to $H_2S$ with and without a pre-treatment step with NaOH and $Ca(OH)_2$ scrubber material.
Figure 14C:
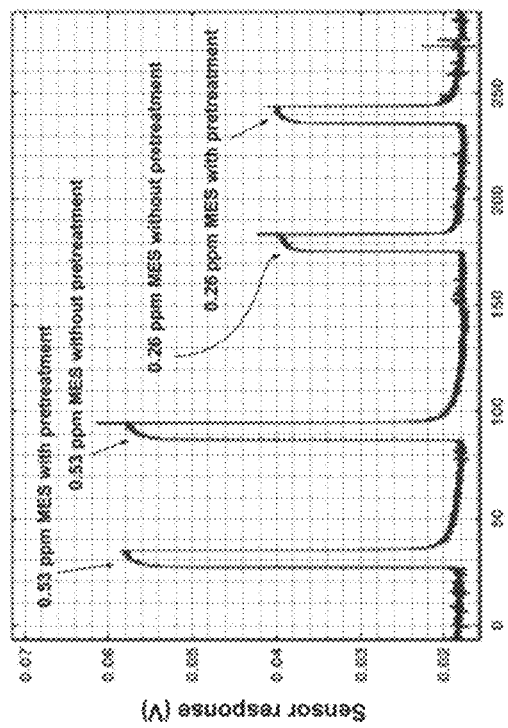
FIG. 14C is a line graph showing electrochemical sensor output in response to MES with and without a pre-treatment step with NaOH and $Ca(OH)_2$ scrubber material.

FIGS. 14A to 14C show the sensor response (voltage) over time to gas samples containing TBM, $H_2S$, and MES, respectively, with and without a scrubbing (pre-treatment) step with the NaOH and $Ca(OH)_2$ scrubber material. As shown in FIGS. 14A and 14B, both TBM and $H_2S$ are substantially removed from the gas by the scrubbing step. As shown in FIG. 14C, MES remains in the gas following scrubbing and little to no MES is lost during the scrubbing step. Thus, the experimental system was able to provide an accurate concentration of the MES present in the gas.

FIGS. 15A and 15B show the sensor response (voltage) over time to a gas sample comprising $H_2S$, with or without a scrubbing step with the $CaCO_3$ scrubber material and with or without the scrubbing step with the MDEA scrubber material, respectively. As shown in FIGS. 15A and 15B, the $H_2S$ is substantially removed by the scrubbing step with the $CaCO_3$ scrubber material and completely removed with the MDEA scrubber material.

FIG. 16 shows the sensor response (voltage) of the system described in FIG. 11 in sensing the TBM and MES content of a gas sample containing TBM, $H_2S$, and MES. The sensing peak at 16-28 min is the MES response, where the sample gas is scrubbed with the NaOH and $Ca(OH)_2$ scrubber material, and the sensing peak at 36-50 min is the total response of MES and TBM, where the sample gas is scrubbed by the MDEA scrubber material. Thus, the experimental system 10 can be used to determine the concentrations of both MES and TBM in a gaseous mixture.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements.

The invention claimed is:

1. A system for analyzing a hydrocarbon gas containing hydrogen sulfide ($H_2S$), mercaptans, and one or more other sulfur compounds, the system comprising:
    a branched fluid conduit that comprises a first branch and a second branch, wherein the branched fluid conduit splits the hydrocarbon gas into a first gas stream that flows through the first branch and a second gas stream that flows through the second branch;
    a first scrubber that receives the first gas stream from the first branch, the first scrubber comprising a first non-aqueous scrubber material that removes the $H_2S$ from the first gas stream to produce a first scrubbed gas, wherein the first non-aqueous scrubber material comprises at least one of a carbonate salt, a bicarbonate salt, a metal oxide, and an amine; and
    a second scrubber that receives the second gas stream from the second branch, the second scrubber comprising a second non-aqueous scrubber material that removes the $H_2S$ and mercaptans from the second gas stream to produce a second scrubbed gas, wherein the second non-aqueous scrubber material comprises at least one of an alkali metal hydroxide, an alkaline earth metal hydroxide, and an iodate salt;
    at least one gas sensor in fluid communication with the first scrubber and the second scrubber, the at least one gas sensor sensing at least one sulfur compound of the one or more other sulfur compounds in the first scrubbed gas and the second scrubbed gas.

2. The system of claim 1, wherein the first scrubber material is the amine and the amine is in liquid-phase.

3. The system of claim 1, wherein the at least one gas sensor comprises a first gas sensor and a second gas sensor, the first gas sensor fluidly connected to the first scrubber and the second gas sensor fluidly connected to the second scrubber.

4. The system of claim 1, further comprising a valve in fluid communication with the first and second scrubbers and the at least one gas sensor, the valve selectively movable between a first position in which a first gas stream flows from the first scrubber to the at least one gas sensor and a second position in which a second gas stream flows from the second scrubber to the at least one gas sensor.

5. The system of claim 1, further comprising at least one pump operable to move the first scrubbed gas and the second scrubbed gas from the first and second scrubber to the at least one gas sensor.

6. The system of claim 1, further comprising a processor that processes sensor output of the at least one gas sensor to determine a concentration of the at least one other sulfur compound.

7. The system of claim 1, wherein the at least one gas sensor comprises one or more electrochemical cells.

8. A method for analyzing a hydrocarbon gas containing hydrogen sulfide ($H_2S$), mercaptans, and two or more other sulfur compounds, the method comprising:
    separating the hydrocarbon gas into a first gas stream and a second gas stream;
    contacting the first gas stream with a first non-aqueous scrubber material to remove the $H_2S$ from the first gas stream to produce a first scrubbed gas stream, wherein the first non-aqueous scrubber material comprises at least one of a carbonate salt, a bicarbonate salt, a metal oxide, and an amine;
    contacting the second gas stream with a second non-aqueous scrubber material to remove the $H_2S$ and mercaptans from the second gas stream to produce a second scrubbed gas stream, wherein the second non-aqueous scrubber material comprises at least one of an alkali metal hydroxide, an alkaline earth metal hydroxide, and an iodate salt;
    sensing at least one first sulfur compound of the two or more other sulfur compounds in the first scrubbed gas stream; and
    sensing at least one second sulfur compound of the two or more other sulfur compounds in the second scrubbed gas stream.

9. The method of claim 8, wherein the second non-aqueous scrubber material comprises the alkali metal hydroxide, the alkaline earth metal hydroxide, or a combination thereof.

10. The method of claim 9, wherein the second non-aqueous scrubber material comprises a mixture of NaOH and $Ca(OH)_2$.

11. The method of claim 8, wherein sensing the at least one first sulfur compound comprises sensing at least one of tetrahydrothiophene (THT), tert-butyl mercaptan (TBM), methyl ethyl sulfide (MES), n-propyl mercaptan (NPM), isopropyl mercaptan (IPM), dimethyl sulfide (DMS), sec-butyl mercaptan (SBM), diethyl sulfide (DES), and ethyl mercaptan (EM).

12. The method of claim 8, wherein sensing the at least one second sulfur compound comprises sensing at least one of MES, DMS, DES, and THT.

13. The method of claim 8, wherein sensing the at least one first sulfur compound comprises generating a first sensor output and sensing the at least one second sulfur compound comprises generating a second sensor output.

14. The method of claim 13, further comprising subtracting the second sensor output from the first sensor output to determine the concentration of one sulfur compound of the at least one first sulfur compound.

15. The system of claim 1, wherein the second non-aqueous scrubber material comprises the alkali metal hydroxide, the alkaline earth metal hydroxide, or a combination thereof.

16. The system of claim 15, wherein the second non-aqueous scrubber material comprises a mixture of NaOH and $Ca(OH)_2$.

* * * * *